US007967752B2

(12) United States Patent
Ocvirk et al.

(10) Patent No.: US 7,967,752 B2
(45) Date of Patent: Jun. 28, 2011

(54) SENSOR SYSTEM AS WELL AS AN ARRANGEMENT AND METHOD FOR MONITORING A CONSTITUENT AND IN PARTICULAR GLUCOSE IN BODY TISSUE

(75) Inventors: Gregor Ocvirk, Mannheim (DE); Helmut Rinne, Hamburg (DE); Arnulf Staib, Heppenheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 452 days.

(21) Appl. No.: 11/425,020

(22) Filed: Jun. 19, 2006

(65) Prior Publication Data
US 2006/0287591 A1  Dec. 21, 2006

(30) Foreign Application Priority Data

Jun. 17, 2005  (EP) .................................. 05013063

(51) Int. Cl.
*A61B 5/00* (2006.01)
(52) U.S. Cl. ......... 600/365; 600/345; 600/347; 600/584
(58) Field of Classification Search .................. 600/365, 600/345, 347, 346, 584, 309, 316, 322, 327, 600/332, 333, 354, 373, 486, 578; 204/400, 204/401, 403.1–403.15, 435, 436
See application file for complete search history.

(56) References Cited

U.S. PATENT DOCUMENTS

| 5,269,891 | A  | * | 12/1993 | Colin ........................... 205/777.5 |
| 5,586,553 | A  |   | 12/1996 | Halili et al. |
| 6,558,351 | B1 |   | 5/2003  | Steil et al. |
| 7,169,117 | B2 | * | 1/2007  | Allen ............................ 600/584 |
| 7,415,299 | B2 | * | 8/2008  | Zimmermann et al. ...... 600/345 |
| 7,445,766 | B2 | * | 11/2008 | Santini et al. .................. 424/9.1 |
| 2002/0022782 | A1 | * | 2/2002 | Kiepen et al. ................. 600/486 |
| 2002/0137998 | A1 |   | 9/2002 | Smart et al. |
| 2003/0125613 | A1 |   | 7/2003 | Enegren et al. |
| 2003/0130616 | A1 | * | 7/2003 | Steil et al. ........................ 604/66 |
| 2004/0176732 | A1 | * | 9/2004 | Frazier et al. ................. 604/345 |
| 2005/0033133 | A1 |   | 2/2005 | Kraft |
| 2006/0258959 | A1 | * | 11/2006 | Sode ............................. 600/584 |

FOREIGN PATENT DOCUMENTS

| WO | 81/01794 A1 | 7/1981 |
| WO | 9614026 A1 | 5/1996 |
| WO | 99/65388 A1 | 12/1999 |
| WO | WO 01/93930 A1 | 12/2001 |
| WO | 0239086 A2 | 5/2002 |

OTHER PUBLICATIONS

JP Office Action received Sep. 7, 2009 in counterpart JP application.

* cited by examiner

*Primary Examiner* — Charles A Marmor, II
*Assistant Examiner* — Michael D'Angelo

(57) ABSTRACT

The invention generally relates to a sensor system. In particular to a sensor for glucose monitoring. The invention also also relates to an arrangement and a method for monitoring a constituent and in particular glucose in body tissue using a sensor system.

28 Claims, 2 Drawing Sheets

SENSOR SYSTEM AS WELL AS AN ARRANGEMENT AND METHOD FOR MONITORING A CONSTITUENT AND IN PARTICULAR GLUCOSE IN BODY TISSUE

REFERENCE TO RELATED APPLICATIONS

The present application claims priority to European Patent Application No. 05 013 063.2, filed Jun. 17, 2005, which is hereby incorporated by reference in its entirety.

TECHNICAL FIELD

The invention generally relates to a sensor system. In particular to a sensor for glucose monitoring. The invention also also relates to an arrangement and a method for monitoring a constituent and in particular glucose in body tissue using a sensor system.

BACKGROUND

Body tissue consists of cells and a tissue structure in a liquid environment in which metabolic products are transported between the cells and the blood vessels. For glucose monitoring especially in the case of diabetic patients it is possible to insert a probe into tissue for long periods in order to continuously collect constituents from the tissue fluid by means of diffusion processes and to determine the glucose content in the tissue from the effusate. This can be closely correlated with the blood glucose content without requiring an invasive access to the blood circulation. At the same time it is possible to administer an insulin-containing medication solution depending on the detected glucose concentration in order to thus create a sort of artificial pancreas. In the known system with active substance dosing the construction is very complex and the system inserted into the body tissue is not realized in an integrated and miniaturized design. In particular there is a risk with rigid needle sensors that additional injuries to the surrounding tissue may occur while it remains in the body and as a result of which significant errors may occur in the determination of the analyte concentration.

On this basis the object of the invention is to avoid the disadvantages occurring in the prior art and to enable the determination of a constituent in the surrounding matrix and passage of a liquid in a simple manner using an implantable device and an appropriate method.

SUMMARY

The invention is generally based on the idea of integrating a sensor and a separate liquid passage on a substrate. Accordingly, it is proposed according to the invention that the sensor is arranged on the support separately from the fluid channel for a direct contact with the body tissue. Information on a constituent can thus be obtained directly from the tissue outside of the liquid that is fed in and out. This enables an optimization of the response time and overall time behavior of the system while simplifying the manufacture due to the integrated design. In addition, storage, transport and collection of perfusion fluids is also dispensed with allowing a substantial reduction in the size of the system especially for applications that can be carried on the body.

In order to make a direct contact with the body tissue i.e. with the cells, the vessels and the supporting matrix, the sensor is located on a surface of the support that is in contact with the body tissue in the inserted state.

The sensor is designed to detect the constituent substantially independently of the amount of extracellular fluid that is present. Hence the sensor responds to an analyte without a measuring volume having to be previously completely filled with liquid at the local site of measurement.

The sensor is in contact with the body tissue at a distance from the opening of the fluid channel on the tissue side. This allows various applications to be achieved in a simple manner which require only one puncture site.

In one embodiment of the present invention the sensor system provides a calibration device for the sensor to be located outside body tissue. The calibration device can be loaded with interstitial fluid via the fluid channel, wherein the calibration device has a reference sensor for calibrating the output signals of the sensor. A calibration solution can optionally also be delivered to the calibration device via the fluid channel.

The fluid channel is connected to a pump unit for removing interstitial fluid from the body tissue. In yet another embodiment, the fluid channel is connected to a metering unit for feeding a medication liquid and especially one which contains insulin into the body tissue.

The fluid channel is connected to a conveying device for feeding a calibration solution of known composition into the body tissue.

For a direct acquisition of measured values, the sensor has an active sensor region that can be brought into contact or is in contact with the body tissue. The sensor is designed to continuously detect glucose as the constituent in the interstitial fluid.

The sensor in a multielectrode design has several electrodes arranged on a surface of the support that engages with the body tissue.

In order to make it more comfortable for the test subject to carry and to avoid additional injury to the surrounding tissue while it is being carried, the support consists of a flexible substrate where the fluid channel and sensor are integrated into the substrate. The flexible and blunt-edged support can be inserted into the body tissue by means of an insertion aid.

In order to remove and supply liquid it is proposed that the fluid channel has at least one opening on the tissue side, at least one opening located outside the body tissue and at least one flow path between the openings that is closed or half open on the longitudinal side and is in particular a capillary flow path.

For the production process the fluid channel is integrated into the optionally multi-part support by laser treatment, hot stamping or photolithography.

Another improvements is attained by the fluid channel having a flow cross-section of less than 1 mm$^2$.

In yet another embodiment, the fluid channel flows into the detection area of the sensor on a surface of the support carrying the sensor, or that the fluid channel flows into a part of the support that faces away from or is distant from the sensor which is outside of the detection area of the sensor.

In order to be able to determine a constituent at two different subcutaneous measuring sites at least two single sensors can be provided as a sensor at different distances from a tissue-side opening of the fluid channel.

In yet another embodiment the sensor has a single sensor for an analyte and a single sensor for an active substance that can be passed into the body tissue through the fluid channel.

The invention also concerns an arrangement for monitoring a constituent and especially glucose in body tissue comprising one of the sensor systems described above. In this case the sensor system is coupled to a signal processing unit for the quantitative determination of the constituent. The quantity of liquid which in particular contains insulin that is passed through the fluid channel can be controlled by a control or regulating device.

With regard to the process the object mentioned above is achieved by arranging the sensor on the support separately from the fluid channel and by bringing it into direct contact with the body tissue.

In order to compensate a signal drift, when interstitial fluid is removed via the fluid channel and the constituent is detected by means of a calibration device, and when the sensor that is in contact with the body tissue is calibrated in accordance with the calibration device. It is also possible that a calibration solution having a known concentration of a constituent is delivered via the fluid channel. It is expedient to automatically carry out the calibration at defined time intervals.

The present also provides to regulate or control the liquid transport through the fluid channel as a function of an output signal of the sensor.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present inventions.

DETAILED DESCRIPTION

The following description of the preferred embodiment is merely exemplary in nature and is in no way intended to limit the invention or its application or uses.

Figure 1:
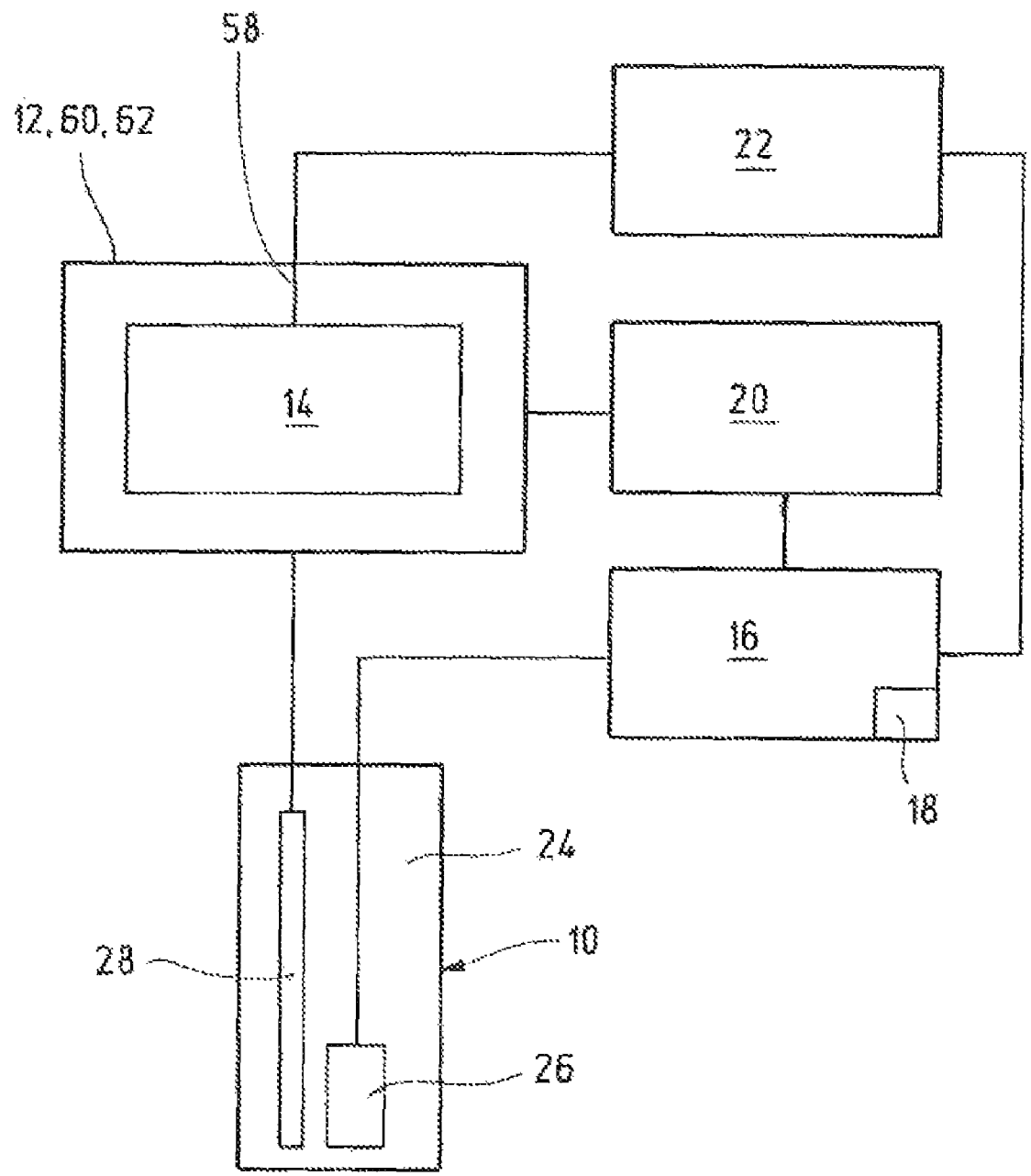
FIG. 1 shows a block diagram of an arrangement for monitoring glucose in body tissue.

The monitoring system shown in FIG. 1 comprises a sensor system 10, a conveying unit 12 with a liquid reservoir 14, a signal processing unit 16 with an alarm trigger 18, a control unit 20 for the conveying unit 12 and a calibration device 22. The arrangement enables constituents (glucose) to be determined in the surrounding matrix by means of the subcutaneously implantable sensor system 10 and allows passage of a liquid.

Figure 2:
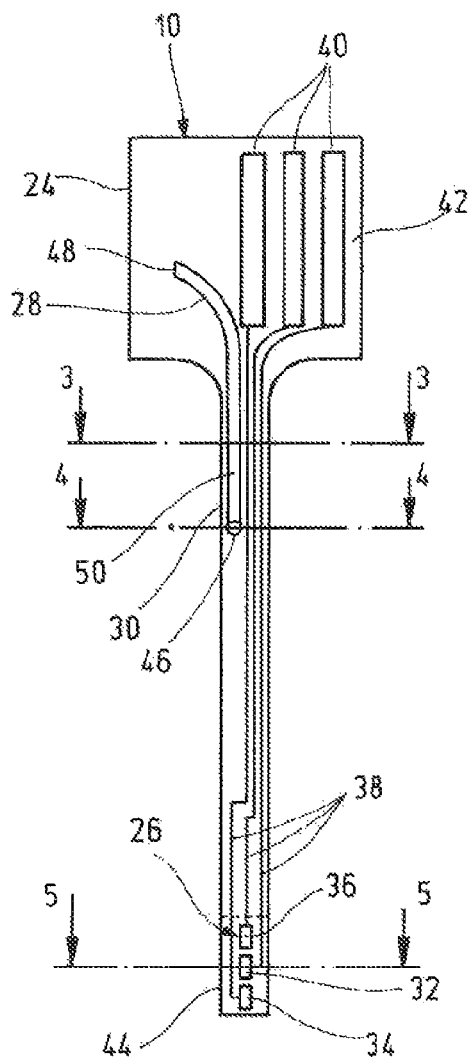
FIG. 2 shows a sensor system arranged according to FIG. 1 in a top-view.

As shown in FIG. 2 the sensor system 10 has a support 24, an electrochemical sensor 26 mounted thereon and an integrated fluid channel 28. The flexible support 24 is for example made from a flexible foil material as a substrate and at least a shaft region 30 thereof can be implanted into body tissue. An insertion aid (not shown) is used for this purpose which creates the necessary tissue opening. It is basically also possible that the support is made of an inflexible material in a needle-like design and can be directly inserted into the body tissue.

The sensor 26 comprises a working electrode 32, a counter electrode 34 and a reference electrode 36. The electrodes are in an electrically conducting contact with associated contact tongues 40 via respective conducting paths 38, said tongues being located on a connecting part 42 of the support 24 that is located outside the body tissue.

The working electrode 32 is characterized as an enzyme electrode in that an intermediate product is formed by the reaction of the analyte (glucose) with a specific enzyme and the intermediate product is converted electrochemically on the working electrode by applying a constant potential between the reference electrode and working electrode. As a result a measurement signal can be detected in a known manner which correlates with the glucose concentration. The potential between the reference electrode and working electrode can be kept constant by means of the reference electrode 36 using a potentiostat to prevent the electrochemical conversion of interfering substances.

The working electrode 322 can be provided with additional layers which serve as a diffusion barrier layer for glucose, as a barrier layer for interfering substances and as a biocompatible layer facing the tissue. The size of the counter electrode 34 is selected such that the current density and thus excess voltage is minimized. There are no constraints on the shape of the electrodes; rectangular or round electrode shapes are can be used. It is also possible that the electrodes intermesh. In each case the free surface of the electrodes forms an active sensor region 44 that can be brought into direct contact with the body tissue, said sensor area being arranged on the support 24 spatially separated from the fluid channel 28. It is also conceivable that several single sensors also have common electrodes in the form of a multielectrode system.

A liquid can be removed from or supplied to the body tissue through the fluid channel 28. For this purpose the fluid channel 28 has at least one opening 46 on the tissue side, at least one opening 48 located outside of the body tissue and at least one flow path 50 between the openings. The side of the flow path 50 is closed and the flow path can have a capillary active cross section of for example less than 1 mm$^2$. Hence the liquid volume contained in the fluid channel 28 can also be kept low.

The opening 46 on the tissue side should be designed such that no significant increase in the hydrodynamic resistance relative to the flow path 50 due to body reactions in this region is detectable during the implantation time. For this purpose it is advantageous to design the surface around this opening 46 in such a manner that its permeability to the analyte or the active substance that is supplied in each case remains essentially unchanged during the period of implantation. For this purpose the physical and chemical properties, the microstructure and the morphology of the surface should be selected such that protein and cell adsorption is kept small. With regard to the chemical properties of the surface, a low surface charge is particularly advantageous.

Figure 3:
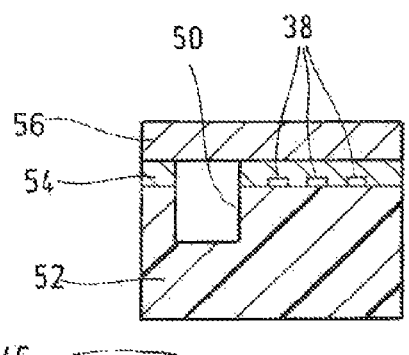
FIG. 3 to 5 show sections along the lines 3-3, 4-4 and 5-5 of FIG. 2.
Figure 4:
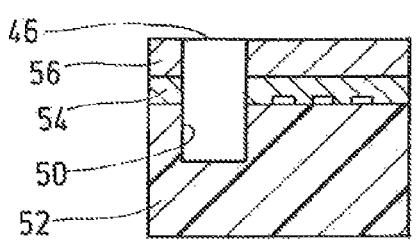
Figure 5:
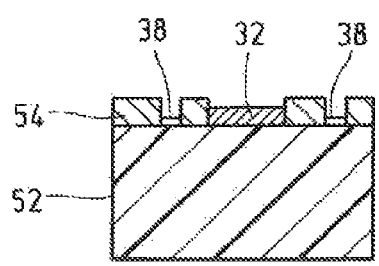

As shown in FIGS. 3 to 5, the support 24 can be composed of multiple layers and in particular consists of a base foil 52, an insulating layer 54 and a cover layer 56. The flow path 50 or rather the liquid passage is produced by laser ablation, hot stamping or photolithography and is closed in a liquid-tight manner by the cover layer 56 with the exception of the openings 46, 48.

In the embodiment shown the subcutaneously implanted glucose sensor 260 is connected via the contact tongues 40 to the extracorporeal signal processing unit 16 in order to display a measuring result to the user that correlates with the glucose content of the interstitial fluid and thus also with the blood glucose and optionally to trigger an alarm via the alarm trigger 18 when it is outside the normoglycaemic range.

In order to carry out an automatic self calibration interstitial fluid can be removed or calibration solution can be supplied via the fluid channel 28 and the downstream conveying unit 12 such that their glucose content or constituent can be determined in parallel by means of the external calibration device 22 or the concentration is known. The calibration device 22 has a reference sensor 58 to which the tissue fluid can be applied. Hence it is possible to automatically carry out a calibration of the output signal of the body sensor 26 that is processed in the signal processing unit 16 at specified time intervals.

Whereas in the previously described embodiment the conveying unit 12 is provided as a pump for removing interstitial fluid, alternatively or in addition thereto a conveying unit 60 may be connected to the fluid channel 28 to feed a calibration solution into the body tissue or a metering unit 62 may be connected to the fluid channel 28 to administer a medication liquid which in particular contains insulin into the body tissue. This also allows the liquid flow rate or the dosage to be adjusted by means of control device 20. Optionally instead of a simple control chain, a closed control loop can be provided for the liquid transport.

The distance of the sensor 26 from the opening 46 of the fluid channel 28 on the tissue side can be varied depending on the composition of the delivered liquid. If a solution of a known analyte content is delivered, the distance should be as small as possible so that a direct change of the measured signal occurs after the liquid flows out from the opening 46. If a solution of an active substance (insulin) is supplied which influences the analyte concentration (glucose) in the tissue, the distance is selected such that at the given pressure difference between the opening 46 and tissue environment, at the given colloid osmotic pressure, at the given time period of liquid supply and at the given diffusion coefficient of the analyte no measurable change in the analyte concentration of the body fluid occurs in the direct vicinity of the sensor.

Another embodiment which is not specifically shown comprises two single sensors for the analyte which are spaced apart, one of the single sensors being located nearer to the tissue-side opening 46. This allows a detection of two different subcutaneous sites which is advantageous due to the inhomogeneity of the subcutaneous tissue and of the respective tissue reaction. Furthermore, when solutions of active substances are delivered via the fluid channel 28, an interaction of the active substance with the surrounding tissue can be determined with the aid of one of the single sensors in order to detect a disease state or for therapeutic monitoring, while the delivery of the solution of active substance can be controlled by means of the other single sensor. Using the said single sensors it is also possible to separately determine an analyte and an active substance fed in via the fluid channel 28. In this case the analyte sensor should be at a greater distance from the opening 46 than the active substance sensor. In addition to determining the analyte concentration, this also enables the active substance to be determined in the surrounding tissue thus allowing a detection of a disease state and therapeutic monitoring.

It is also conceivable that two analyte sensors and one active substance sensor are provided where the first analyte sensor is at a greater distance from the opening 46 on the tissue side than the second analyte sensor and than the active substance sensor.

As shown by numerous studies, a tissue capsule forms around an object implanted in tissue in the process of wound healing. The thickness of the fibrous tissue capsule depends on the size of the object itself. It may be assumed that the fibrous capsule represents a diffusion barrier for an implanted sensor. These problems become particularly pronounced when an adequate amount of a fluid transport medium is necessary to deliver the analyte from the tissue environment to the sensor.

In contrast with the measures according to the invention the success of the measurement does not depend on the amount of interstitial fluid which is hardly present particularly in subcutaneous tissue. Hence the measurement is hardly affected by other influencing factors such as pressure, movement and position of the tissue, which influence the tissue content of interstitial fluid. An insertion set that can be cost-effectively manufactured, that is miniaturized and thus causes minimum damage to the body tissue is created for the improved use of flexible thin layer sensors for measuring constituents in a body tissue. In addition to measurement with an optimized response time it is possible to feed liquids into or out of a separate area of body tissue. This avoids the disadvantages of the prior art and above all the significant measurement errors due to body tissue injury caused by rigid and macroscopic needle sensors and the high manufacturing costs due to the complex construction. In particular it is not necessary to pass through a dialysis fluid because the implanted sensor is directly contacted with the tissue i.e. with the cells, the vessels and the supporting matrix. This makes measurement in interstitial fluid obsolete.

It is noted that terms like "preferably", "commonly", and "typically" are not utilized herein to limits the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A sensor system especially for glucose monitoring, the sensor system comprising:
   a support that can be at least partially inserted into body tissue;
   a fluid channel integrated on the support for passing through an interstitial fluid;
   a sensor that responds to a constituent of the body tissue, wherein the sensor is integrated on the support and configured for direct contact with the body tissue separately from the fluid channel;
   a signal processor electrically coupled to the sensor for generating a measurement result;
   a calibration device configured to be located outside the body tissue to calibrate an output signal of the sensor, the calibration device having a reference sensor that is fluidly coupled to the fluid channel for passing through the interstitial fluid and electrically coupled to the signal processor; and a pumping unit for removing interstitial fluid not in contact with the sensor through the fluid channel and into the calibration device for use in calibrating the sensor.

2. The sensor system according to claim 1, wherein the sensor is arranged on a surface of the support which, when inserted, is in contact with the body tissue.

3. The sensor system according to claim 2, wherein the sensor in a multielectrode configuration has several electrodes arranged on the surface of the support which engages with the body tissue.

4. The sensor system according to claim 1, wherein the sensor responds directly to the constituent independently of the amount of the locally present tissue fluid.

5. The sensor system according to claim 1, wherein the sensor is in direct engagement with the body tissue at a distance axial from an opening of the fluid channel on an active sensor region side.

6. The sensor system according to claim 1, wherein an interstitial fluid and/or a calibration solution can be fed via the fluid channel to the calibration device for the sensor that is located outside of the body tissue.

7. The sensor system according to claim 1, wherein the fluid channel is connected to a metering unit to feed a medication liquid.

8. The sensor system according to claim 7, wherein the medication liquid is insulin.

9. The sensor system according to claim 1, wherein the sensor has an active sensor region that can be brought into contact with the body tissue.

10. The sensor system according to claim 1, wherein the sensor is designed to continuously detect glucose as a constituent in the interstitial fluid.

11. The sensor system according to claim 1, wherein the support is formed by a flexible flat substrate wherein the fluid channel and the sensor are designed as a thin layer structure integrated on the substrate as a composite part.

12. The sensor system according to claim 11, wherein the flexible support can be inserted into the body tissue by means of an insertion aid.

13. The sensor system according to claim 1, wherein the fluid channel has at least one opening on an active sensor region side, at least one opening located outside of the body tissue and at least one flow path between the openings that is a capillary flow path.

14. The sensor system according to claim 1, wherein the fluid channel is integrated into an optionally multi-part support by laser treatment, hot stamping or photolithography.

15. The sensor system according to claim 1 wherein the fluid channel has a flow cross-section of less than 1 mm$^2$.

16. The sensor system according to claim 1, wherein the fluid channel opens onto the surface of the support carrying the sensor in the detection area of the sensor.

17. The sensor system according to claim 1, wherein the fluid channel flows into a part of the support that faces away from or is distant from the sensor and is outside of the detection area of the sensor.

18. The sensor system according to claim 1, wherein the sensor is at least two single sensors that are at different distances from an opening of the fluid channel on the tissue side.

19. The sensor system according to claim 1, wherein the sensor has a single sensor for an analyte and a single sensor for an active substance that can be passed into the body tissue through the fluid channel.

20. The sensor system according to claim 1, wherein the support is partially inserted into a subcutaneous tissue.

21. A method for monitoring a constituent in body tissue, the method comprising:
 inserting a support into body tissue;
 removing interstitial fluid from the body tissue by means of a fluid channel integrated on the support;
 monitoring a constituent of the body tissue with the aid of a sensor wherein the sensor is integrated to the support and configured for direct contact with the body tissue separately from the fluid channel;
 pumping interstitial fluid from the body tissue through the fluid channel into a calibration device for calibrating the sensor; and,
 calibrating an output signal of the sensor using the calibration device located outside the body tissue the calibration device having a reference sensor that is fluidly coupled to the fluid channel and electrically coupled to a signal processor.

22. The method according to claim 21, wherein an interstitial fluid is removed via the fluid channel and the constituent is detected by means of the calibration device.

23. The method according to claim 21, wherein a calibration solution is delivered via the fluid channel and is used to calibrate the sensor that is in contact with the body tissue.

24. The method according to claim 22, wherein the calibration is carried out automatically at specified time intervals.

25. The method according to claim 21, wherein the liquid transport through the fluid channel is controlled or regulated as a function of an output signal of the sensor.

26. The method according to claim 21, wherein an alarm is triggered when the detected concentration of the constituent falls below or exceeds a preset threshold value.

27. The method according to claim 21, wherein an alarm is triggered when the voltage falls below a minimum supply voltage for the sensor system.

28. The method of claim 21, wherein the support is partially inserted into the subcutaneous tissue.

* * * * *